United States Patent
Sohn et al.

(10) Patent No.: US 9,772,315 B2
(45) Date of Patent: Sep. 26, 2017

(54) WIRELESS DIAGNOSIS APPARATUS FOR STRUCTURE USING NONLINEAR ULTRASONIC WAVE MODULATION TECHNIQUE AND SAFETY DIAGNOSIS METHOD USING THE SAME

(71) Applicant: KOREA ADVANCED INSTITUTE OF SCIENCE AND TECHNOLOGY, Daejeon (KR)

(72) Inventors: Hoon Sohn, Daejeon (KR); Hyung Jin Lim, Daejeon (KR); Su Young Yang, Daejeon (KR); Peipei Liu, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 170 days.

(21) Appl. No.: 14/787,127

(22) PCT Filed: Dec. 23, 2013

(86) PCT No.: PCT/KR2013/012037
§ 371 (c)(1),
(2) Date: Oct. 26, 2015

(87) PCT Pub. No.: WO2014/178518
PCT Pub. Date: Nov. 6, 2014

(65) Prior Publication Data
US 2016/0109416 A1 Apr. 21, 2016

(30) Foreign Application Priority Data
Apr. 30, 2013 (KR) ........................ 10-2013-0048072

(51) Int. Cl.
*G01N 29/04* (2006.01)
*G01N 29/06* (2006.01)
(Continued)

(52) U.S. Cl.
CPC ............. *G01N 29/46* (2013.01); *G01B 17/04* (2013.01); *G01M 5/0033* (2013.01);
(Continued)

(58) Field of Classification Search
CPC ............. G01M 5/0066; G01M 5/0033; G01N 29/0654; G01N 29/28; G01N 29/045;
(Continued)

(56) References Cited

U.S. PATENT DOCUMENTS 5,824,908 A * 10/1998 Schindel ................ G01N 29/11
73/598
6,186,004 B1 * 2/2001 Kaduchak ............ G01N 29/036
73/596
(Continued)

FOREIGN PATENT DOCUMENTS

JP 2001-337077 A 12/2001
JP 2005-053613 A 3/2005
(Continued)

*Primary Examiner* — J M Saint Surin
(74) *Attorney, Agent, or Firm* — Rabin & Berdo, P.C.

(57) ABSTRACT

The present invention relates to a safety diagnosis method for a structure using a nonlinear ultrasonic wave modulation technique. The safety diagnosis method includes: making the structure vibrate by applying signals of different ultrasonic frequencies; converting the responses of the structure generated by the vibration into digital signals; extracting first modulation signals by subtracting the harmonic responses and the linear responses of the signals of different ultrasonic frequencies from the digital signals and synchronously demodulating the digital signals; constructing a first sideband spectrogram by combining the first modulation signals generated by continuously changing at least frequency among the signals of different ultrasonic frequencies; and deciding whether the structure is cracked based on the first sideband spectrogram. Even though the power of the ultrasonic wave applied to the structure is very small as (Continued)

compared with the related art, whether there is the damage is precisely decided, and thus power consumption may be reduced.

15 Claims, 7 Drawing Sheets

(51) Int. Cl.
  *G01N 29/24*  (2006.01)
  *G01N 29/28*  (2006.01)
  *G01B 17/04*  (2006.01)
  *G01M 5/00*  (2006.01)
  *G01N 29/34*  (2006.01)
  *G01N 29/46*  (2006.01)

(52) U.S. Cl.
  CPC ........ *G01M 5/0066* (2013.01); *G01N 29/045* (2013.01); *G01N 29/0654* (2013.01); *G01N 29/2437* (2013.01); *G01N 29/28* (2013.01); *G01N 29/348* (2013.01); *G01N 2291/01* (2013.01); *G01N 2291/023* (2013.01); *G01N 2291/0258* (2013.01); *G01N 2291/0289* (2013.01); *G01N 2291/02475* (2013.01); *G01N 2291/02491* (2013.01); *G01N 2291/106* (2013.01)

(58) Field of Classification Search
  CPC .. G01N 29/348; G01N 29/46; G01N 29/2437; G01N 2291/0289; G01N 2291/02475; G01N 2291/106; G01N 2291/02491; G01N 2291/0258; G01N 2291/01; G01N 2291/023; G01B 17/04
  USPC .......................................................... 73/577
  See application file for complete search history.

(56) References Cited

U.S. PATENT DOCUMENTS

| | | | |
|---|---|---|---|
| 8,100,015 B2* | 1/2012 | Karasawa | G01N 29/226 73/602 |
| 8,199,931 B1* | 6/2012 | Norris | H04R 17/00 181/142 |
| 8,371,170 B2 | 2/2013 | Masuda | |
| 2009/0133501 A1* | 5/2009 | Georgeson | G01N 29/04 73/632 |
| 2010/0319452 A1 | 12/2010 | Masuda | |

FOREIGN PATENT DOCUMENTS

| | | |
|---|---|---|
| KR | 10-0784582 B1 | 11/2007 |
| KR | 10-2010-0134989 A | 12/2010 |
| KR | 10-1053422 B1 | 8/2011 |
| WO | WO 2009-101978 A1 | 8/2009 |

\* cited by examiner

WIRELESS DIAGNOSIS APPARATUS FOR STRUCTURE USING NONLINEAR ULTRASONIC WAVE MODULATION TECHNIQUE AND SAFETY DIAGNOSIS METHOD USING THE SAME

TECHNICAL FIELD

The present invention relates to a wireless diagnosis apparatus for a structure, and more particularly, to a wireless diagnosis apparatus for the structure using a nonlinear ultrasonic wave modulation technique capable of precisely detecting structural damages based on a linear response subtraction technique and a first sideband spectrogram construction.

BACKGROUND ART

In general, facilities of basic industries, which include bridges, large-scale facilities, underground facilities, and the like have been gradually enlarged and advanced to meet various demands of social members. As a result, various new technologies, new construction methods, new materials, and the like have been introduced and the need for verification of safety and the like as prerequisites for introducing the new technologies has been required. Further, the number of superannuated structures which were built several decades ago has gradually increased and there is a trend that introduction of a precision safety diagnosis technology for evaluating a current state of the structure or an instrumentation system for maintenance is accelerated.

A safety diagnosis management system of social infrastructure facilities is generally executed by performing a nondestructive inspection by an inspector having a safety inspection certificate. However, since the safety diagnosis inspection is periodically performed, the safety diagnosis inspection has problems in that it is difficult to sense damage immediately, the structure shutdowns while inspection and inspection costs including labor costs are large because the structure needs to be inspected by inspectors. Further, approximately 90% of damage of metallic structures occurs by a fatigue crack and the fatigue crack starts from a small size which is invisible to the naked eye and only when the fatigue crack reaches 80% of a total fatigue crack cycle, the fatigue crack becomes conspicuous by the existing damage sensing method. If the fatigue crack is enlarged, the cost for restoring it increases accordingly.

Korean Patent Registration No. 0784582 (registered on Dec. 4, 2007) relates to a technology regarding apparatus and method for measuring the damage of a structure using piezoelectric devices, but has a problem in that it cannot precisely sense whether a crack occurs when supplied power is low.

SUMMARY OF INVENTION

Technical Problem

An object of the present invention is to provide a wireless diagnosis apparatus for a structure using a nonlinear ultrasonic wave modulation technique capable of extracting first modulation signals by a linear response subtraction technique and a synchronous demodulation technique, constructing a first sideband spectrogram by combining the generated first modulation signals while changing a frequency of an ultrasonic wave, and diagnosing whether the structure is cracked from the first sideband spectrogram.

Solution to Problem

According to an aspect of the present invention, a safety diagnosis method for a structure using a nonlinear ultrasonic wave modulation technique includes: making the structure vibrate by applying signals of different ultrasonic frequencies; converting the responses of the structure generated by the vibration into digital signals; extracting first modulation signals by subtracting the harmonic responses and the linear responses of the signals of different ultrasonic frequencies from the digital signals and synchronously demodulating the digital signals; constructing a first sideband spectrogram (FSS) by combining the first modulation signals generated by changing at least frequency among the signals of different ultrasonic frequencies; and deciding whether the structure is cracked based on the first sideband spectrogram.

According to another aspect of the present invention, a method for measuring a fatigue crack of a structure using a nonlinear ultrasonic wave modulation technique includes: applying one of ultrasonic waves of different ultrasonic frequencies to the inside of a concentric dual piezoelectric transducer attached to the structure and applying the other one ultrasonic wave to the outside of the concentric dual piezoelectric transducer to make the structure vibrate; converting the responses of the structure generated by the vibration into first digital signals; converting the responses of the structure generated by applying only the one ultrasonic wave to the concentric dual piezoelectric transducer into second digital signals; converting the responses of the structure generated by applying only the other one ultrasonic wave to the concentric dual piezoelectric transducer into third digital signals; and deciding whether the structure is cracked through synchronous demodulation of signals acquired by removing the second digital signals and the third digital signals from the first digitals signals.

According to yet another aspect of the present invention, a system for measuring a fatigue crack of a structure using a nonlinear ultrasonic wave modulation technique includes: a high-frequency generation unit generating an ultrasonic wave of a high frequency according to a first control signal; a low-frequency generation unit generating an ultrasonic wave of a low frequency according to a second control signal; a first piezoelectric transducer attached to the structure to apply the ultrasonic wave of the low frequency to the structure; a second piezoelectric transducer attached to the structure to apply the ultrasonic wave of the high frequency to the structure; a third piezoelectric transducer converting responses of the structure generated by the ultrasonic waves into electric signals; a digitizer converting an output of the third piezoelectric transducer into digital signals; a control unit controlling activation timings of the first control signal and the second control signal; and a digital signal processing unit subtracting linear responses and harmonic responses from an output of the digitizer and synchronously demodulating the corresponding responses to output the synchronously demodulated responses as fatigue crack information of the structure.

According to still another aspect of the present invention, a wireless diagnosis apparatus for a structure using a nonlinear ultrasonic wave modulation technique includes: a frequency generation unit outputting a pumping signal and a probing signal of different ultrasonic frequencies; a piezoelectric transducer unit making vibration by applying the pumping signal and the probing signal to the structure and outputting responses of the structure as electric signals; a digitizer converting an output of the piezoelectric transducer unit into digital signals; a digital signal processing unit constructing a first sideband spectrogram through linear response subtraction and synchronous demodulation of an output of the digitizer; and a wireless transmission unit wirelessly transmitting the first sideband spectrogram to an inspection system of a remote place.

Advantageous Effects of Invention

According to the embodiment of the present invention, since the damage of the structure may be sensed during its operation, it is possible to sense initially a fatigue crack and prevent a crack of the structure from being increased in advance by wirelessly transmitting the diagnosis result to an inspection system at a remote place.

Further, since the safety inspection is performed in real time by wireless transmission of the diagnosis result of the structure, it is possible to largely reduce inspection costs according to human resources.

According to the specific signal processing method and the measurement method according to the present invention, since whether there is the damage can be precisely decided even though the low voltage level of the applied ultrasonic wave compared with the related art by discovering a proper frequency capable of precisely deciding whether there is the damage and vibrating the ultrasonic wave of the corresponding frequency to the structure to diagnose the damage, it is possible to largely reduce power consumption of the diagnosis apparatus.

Further, since the fatigue crack is initially sensed and the crack is prevented from increasing in advance, it is possible to extend a lifetime of an infra-structure, an airplane, a train, or the like and ensure safety of the facilities.

Further, precise diagnosis is possible even in the low-power supply and the diagnosis sensor may be decreased. Therefore, the present invention may be widely used without being limited to the size of the diagnosis sensor.

BRIEF DESCRIPTION OF DRAWINGS

FIG. 1(a) illustrates there is no fatigue damage to a metal structure as a frequency response. FIG. 1(b) illustrates there is the fatigue damage to a metal structure as a frequency response.

FIGS. 2(a) and 2(b) are the fitting-lug used in the test. FIG. 2(c) illustrates a repeated load testing machine for simulating the fatigue damage. FIG. 2(d) illustrates a specimen in which a fatigue damage having a length of about 40 mm is generated by the repeated load.

FIGS. 5(a) and 5(b) illustrate results obtained by analyzing the signal output from a structure with the damage and a structure without the damage in the time-frequency domain. FIGS. 5(c) and 5(d) illustrate results obtained by analyzing the output of the digitizer and the LRS-processed signal in the LRS unit in the time-frequency domain. FIGS. 5(e) and 5(f) illustrate signals in which only the first modulation signals are extracted from the output of the digitizer by applying the SD method after the LSR technique to the response of the structure.

FIGS. 6(a) and 6(c) illustrate a measured result of the measurement system illustrated in FIG. 4. FIGS. 6(b) and 6(d) illustrate results of generating the FSS by continuously changing the pumping signal and the probing signal.

FIGS. 7(a), 7(b), 7(c), and 7(d) illustrate results measured when the frequency 50 to 150 kHz of the pumping signal and the frequency 400 to 500 kHz of the probing signal are increased for the cases of FIGS. 6(a), 6(b), 6(c), and 6(d), respectively.

DESCRIPTION OF EMBODIMENTS

Hereinafter, detailed embodiments of the present invention will be described with reference to the accompanying drawings. In the illustrated drawings, since only core matters are enlarged and illustrated for clarity and subsidiary matters are omitted, it should not be interpreted that the present invention is not limited to the drawings.

The present invention senses nonlinearity generated in a structure due to a damage for the damage diagnosis. The present invention may diagnose structural damages based on a first sideband spectrogram (hereinafter, referred to as an "FSS") by a linear response subtraction (hereinafter, referred to as "LRS") method, synchronous demodulation (hereinafter, referred to as "SD"), and the FSS of a modulation component sensed in the structure by irradiating ultrasonic waves having different ultrasonic frequencies to the structure, inspect whether the structure is cracked in real time by wirelessly transmitting the diagnosis result to an inspection system at a remote place, and prevent the crack of the structure from being largely generated in advance.

Figure 1:
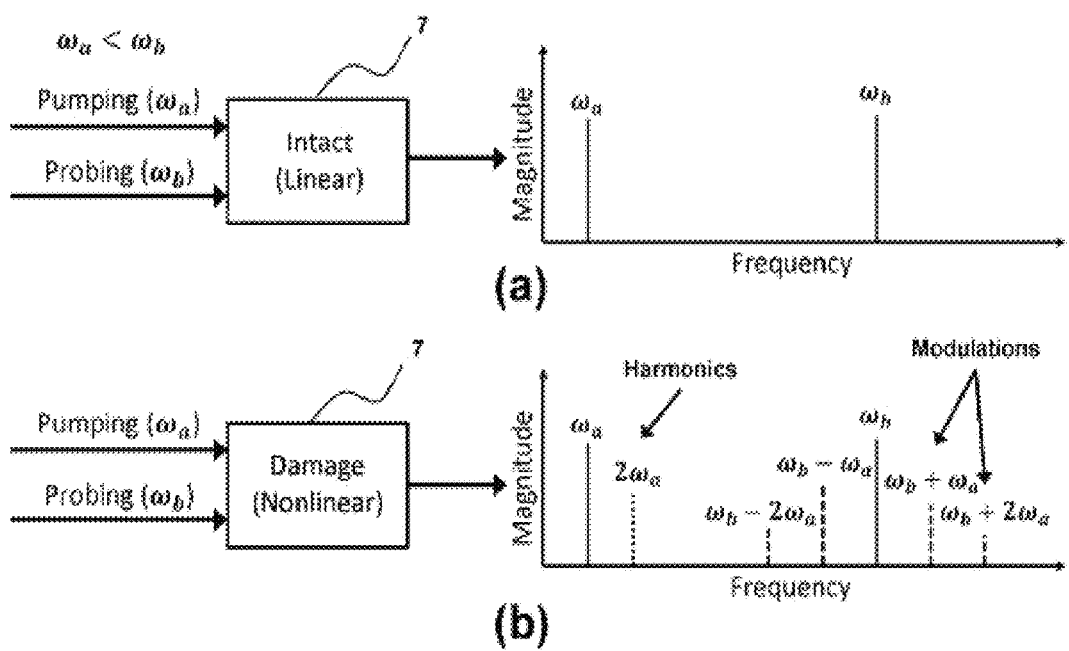
FIG. 1 illustrates a frequency response characteristic according to whether a structure is damaged or not.

FIGS. 1(a) and 1(b) illustrate a frequency characteristic according to whether the structure is damaged, and as illustrated in FIG. 1(a), in the case where there is no fatigue damage to a metal structure, as a frequency response, only signals of two ultrasonic waves are measured by irradiating the ultrasonic wave to the structure. However, as illustrated in FIG. 1(b), in the case where there is the fatigue damage to a metal structure, since a damage area locally has non-linearity, harmonics and modulation of the frequency component of the ultrasonic wave are additionally generated when the ultrasonic wave passes through the corresponding damage area. Unlike the related art, the present invention vibrates two ultrasonic waves having different ultrasonic frequencies to the structure, generates the FSS by extracting first modulation components by the LRS method and the SD method from a signal response generated from the damage area and combining the first modulation components having different values according to a frequency variable of the ultrasonic waves, and diagnoses the fatigue damage of the structure from the FSS.

Figure 2:
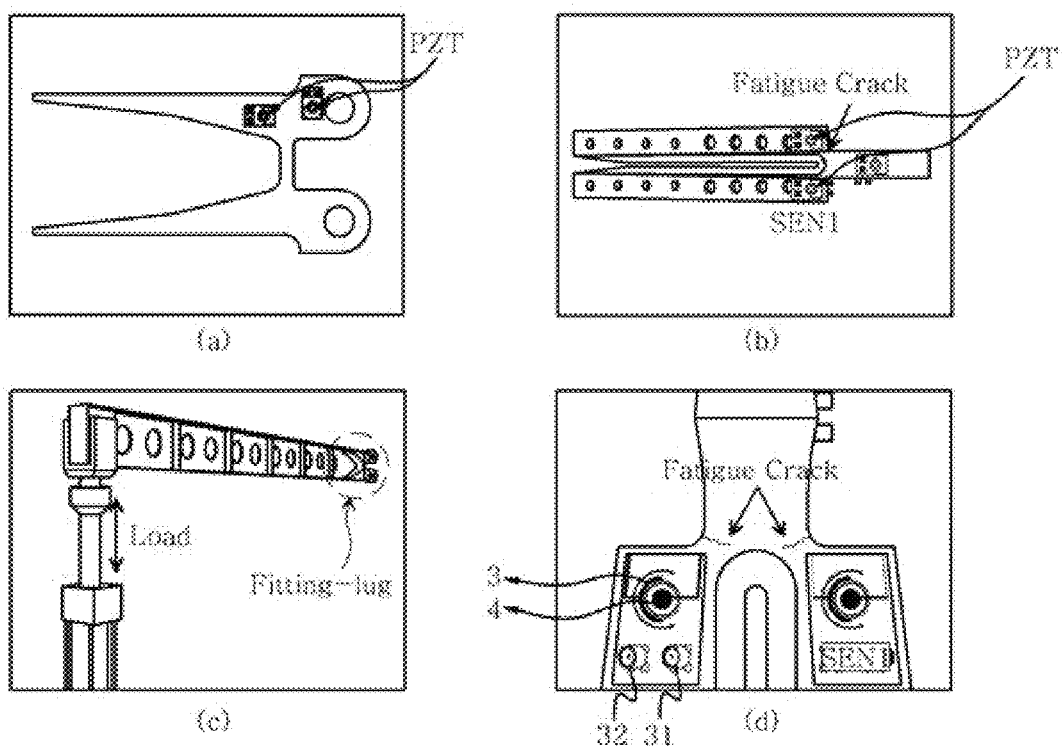
FIG. 2 illustrates a mock-up of a fitting-lug structure for connecting a fuselage and wings of an airplane used in the present invention.

As illustrated in FIG. 2, the present invention is a result obtained by testing a mock-up of a fitting-lug structure connecting a fuselage and wings of an airplane. FIGS. 2(a) and 2(b) are the fitting-lug used in the test, and FIG. 2(c) is a repeated load testing machine for simulating the fatigue damage. As illustrated in FIGS. 2(a) and 2(b), concentric dual piezoelectric transducers are attached to the fitting-lug. A pumping signal of a low frequency is applied to a piezoelectric transducer 3 outside the concentric dual piezoelectric transducer (ACT), a probing signal of a high frequency is vibrated through a second piezoelectric transducer 4 inside the ACT, and response signals are simultaneously measured from the insides of two piezoelectric transducers attached to the other side of the ACT. FIG. 2(c) is a model in which a specimen is installed on equipment capable of adding the repeated load corresponding to 1,000 hours which is a flight time of an actual airplane and FIG. 2(d) illustrates a specimen in which a fatigue damage having a length of about 40 mm is generated by the repeated load.

Figure 3:
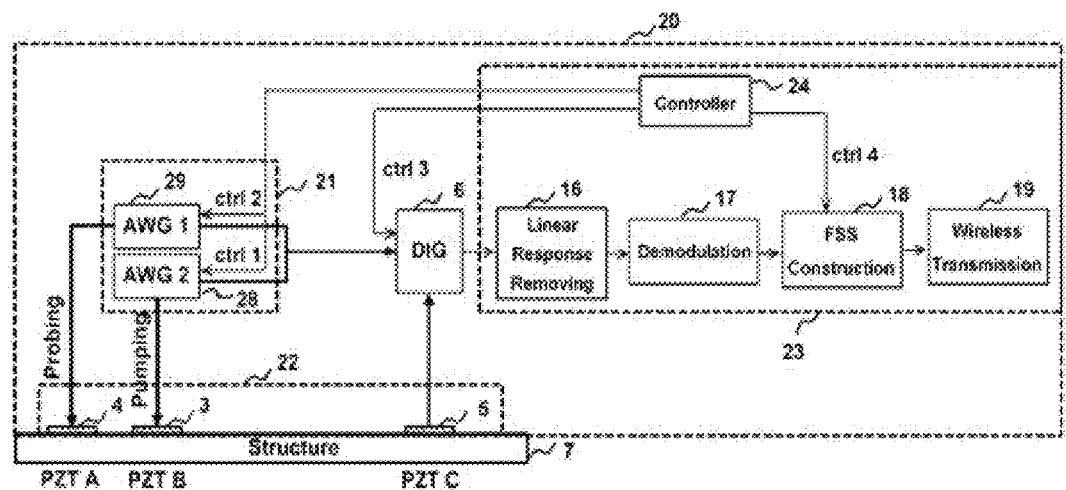
FIG. 3 is a block diagram of a wireless diagnosis apparatus for a structure using a nonlinear ultrasonic wave modulation technique according to the present invention.

FIG. 3 illustrates a wireless diagnosis apparatus 20 using a nonlinear ultrasonic wave modulation technique according to the present invention and the wireless diagnosis apparatus 20 may diagnose a fatigue crack such as the structure illustrated in FIG. 2. The wireless diagnosis apparatus 20 includes a ultrasonic frequency generation unit 21 constituted by a low frequency generation unit 28 and a high frequency generation unit 29 outputting different ultrasonic frequency signals, a piezoelectric transducer unit 22 vibrating the structure by receiving the low frequency and the high frequency from the low frequency generation unit 28 and the high frequency generation unit 29 and sensing an ultrasonic wave from the structure, a digitizer converting output of the piezoelectric transducer unit 22 into a digital signal, and a digital signal processing unit 23 extracting first modulation components by processing the LRS and the SD, generates the FSS from the combining of the first modulation components generated by varying the frequency of the ultrasonic wave, diagnosing a crack from the FSS, and wirelessly transmitting the diagnosis result to an inspector or an inspection system.

For example, the high frequency is an ultrasonic wave of 80 kHz to 110 kHz and called a probing signal. The low frequency is an ultrasonic wave of 10 kHz to 20 kHz and called a pumping signal. The low frequency generation unit 28 generates the pumping signal as the low frequency according to a first control signal ctrl1. For example, the pumping signal is a sine wave of 16.5 kHz and 12 V. The high frequency generation unit 29 generates the probing signal as the high frequency according to a second control signal ctrl2. For example, the probing signal is a linear chirp signal of 12 V having a frequency band of 80 kHz to 110 kHz. Even though a voltage level of the ultrasonic wave used in the present invention is very small as compared with the related art, whether the damage exists is diagnosed and thus, a wireless diagnosis sensor with low power consumption may be implemented. The low frequency generation unit 28 and the high frequency generation unit 29 may be implemented by a digital-analogue converter. In addition, the low frequency generation unit 28 and the high frequency generation unit 29 may further include filters and amplifiers.

When describing the component of FIG. 3 in detail, the piezoelectric transducer unit 22 includes a first piezoelectric transducer 3 vibrating the low frequency to the structure, a second piezoelectric transducer 4 vibrating the high frequency to the structure, and a third piezoelectric transducer 5 outputting a response of the structure by the low frequency and the high frequency to an electric signal.

The first piezoelectric transducer 3 and the second piezoelectric transducer 4 are attached to the structure to apply the ultrasonic waves having different ultrasonic frequencies to the structure and cause vibration and may be implemented by using the ACT illustrated in FIGS. 2(a), 2(b), and 2(d). The ACT is constituted by two piezoelectric transducers having the same center, one (the first piezoelectric transducer 3) is a circular sensor at the center and the other (the second piezoelectric transducer 4) is a ring-shaped sensor formed to be spaced apart from the circular sensor at a predetermined distance. Referring to FIG. 2(d), in the first piezoelectric transducer 3, the low frequency is applied through a first input terminal 31 and in the second piezoelectric transducer 4, the high frequency is applied through a second input terminal 32. When the ACT is used, even though the ultrasonic wave is applied at different positions, the same effect as being applied at the same position is exhibited.

The third piezoelectric transducer 5 is attached to a structure 7 to convert a response generated in the structure 7 into an electric signal by vibration.

The digitizer 6 measures an output of the third piezoelectric transducer 5 according to a third control signal ctrl3 and converts the output of the third piezoelectric transducer 5 having an analogue single form into a digital signal. The digitizer 6 may be implemented by an analogue-digital converter and may further include filters and amplifiers.

The output of the high frequency generation unit 29 and the low frequency generation unit 28 is applied to the first piezoelectric transducer 3 and the second piezoelectric transducer 4 and the output of the third piezoelectric transducer 5 is applied to the digitizer 6. The high frequency generation unit 29, the low frequency generation unit 28, the digitizer 6, and the piezoelectric transducers 3, 4, and 5 are connected to each other by a cable, a transmission line, or the like.

The digital signal processing unit 23 extracts first modulation signals by processing the LSR and the SD from the response generated in the structure by the frequency signals, generates the FSS to decide whether the structure is damaged, and transmit the diagnosis result to a safety management inspector or inspection system positioned at a remote place. The digital signal processing unit 23 includes a LSR unit 16, an SD unit 17, a FSS generation unit 18, and a wireless transmission unit 19.

The LSR technique is a specific signal processing method of only the present invention as a method of subtracting a response of the structure when the pumping signal and the probing signal are separately vibrated from the response of the structure when the pumping signal and the probing signal are simultaneously vibrated.

The LSR technique will be described below in detail. The response of the structure generated when the pumping signal and the probing signal are simultaneously vibrated to the structure is converted into an analogue electric signal by the third piezoelectric transducer 5, and the digitizer 6 converts the analogue electric signal into the first digital signal. In addition, in order to subtract the linear responses and the harmonic responses of the pumping signal and the probing signal, in this case, the third piezoelectric transducer 5 and the digitizer 6 convert the response of the structure generated by vibrating only the pumping signal to the structure into the second digital signal. Next, the third piezoelectric transducer 5 and the digitizer 6 convert the response of the structure generated by vibrating only the probing signal to the structure into the third digital signal. The LRS unit 16 subtracts the second digital signal and the third digital signal from the first digital signal. Here, it is assumed that there is no error due to a difference between times when the respective frequency signals are applied. Accordingly, referring to FIG. 5(d), the LRS unit 16 may extract only the signal of the sideband from the output of the digitizer.

$$u^{(3)} = u^T - (u^{(1)} + u^{(2)}) \quad (1)$$

$$\hat{u}^{(3)} = u_{b \pm a} e^{i((\kappa_b \pm \kappa_a)z - (\omega_b \pm \omega_a)t + (\theta_b \pm \theta_a))} + \alpha(u^{(1)} + u^{(2)}) + c.\ c,$$
$$\alpha \approx 0 \quad (2)$$

Figure 8:
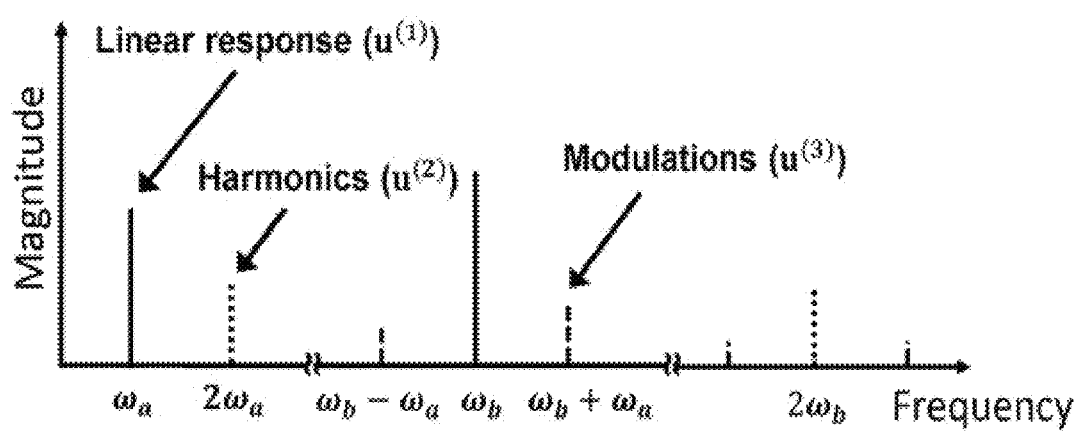
FIG. 8 is a diagram for describing a linear response subtraction processing technique according to the present invention.

Referring to FIG. 8, the LSR unit 16 may subtract a linear response $u^{(1)}$ and subtract a harmonic response $u^{(2)}$ from the signals in the entire frequency band from an output signal $u^{(T)}$ from the structure and generate only a signal $u^{(3)}$ of the sideband as Equation 1. Alternatively, the LSR unit 16 may obtain the sideband signal in which the error generated in an actual situation through the LRS processing by applying Equation 2. The signal $u^{(3)}$ of Equation 1 is a theoretically available LSR-processed value, and a signal $\hat{u}^{(3)}$ of Equation 2 is a value LSR-processed by considering the errors generated in the actual situation.

The SD unit 17 synchronously demodulates the output of the LSR unit 16. The SD method is a signal processing method used in general communication.

The control unit 24 varies output frequencies of the low frequency generation unit 28 and the high frequency generation unit 29 and controls a signal output timing of the low frequency generation unit 28 and the high frequency generation unit 29 so that both the low frequency and the high frequency are applied to the structure, only the low frequency is applied, or only the high frequency is applied. The control unit 24 selects a frequency outputting a first modulation signal having the largest value from the FSS to set the frequency as the frequency of the pumping signal and the probing signal.

The FSS generation unit 18 extracts only the first modulation signal by receiving the output signal of the SD unit 17 according to a frequency variable of the high frequency and the low frequency to generate the FSS according to a fourth control signal ctrl4. The control unit 24 generates the FSS by combining the first modulation components extracted from the SD unit 17 with each other in the FSS generation unit 18 when varying the frequencies output from the low frequency generation unit 28 and the high frequency generation unit 29.

The wireless transmission unit 19 wirelessly transmits the output of the FSS generation unit 18 to the inspector or inspection system positioned at the remote place to immediately verify whether there is a fatigue crack of the structure. The wireless transmission unit 19 transmits data by a wireless communication scheme such as code division multiple access (CDMA), Zigbee, Bluetooth, WiFi, wireless broadband internet, and world interoperability for microwave access.

Figure 5:
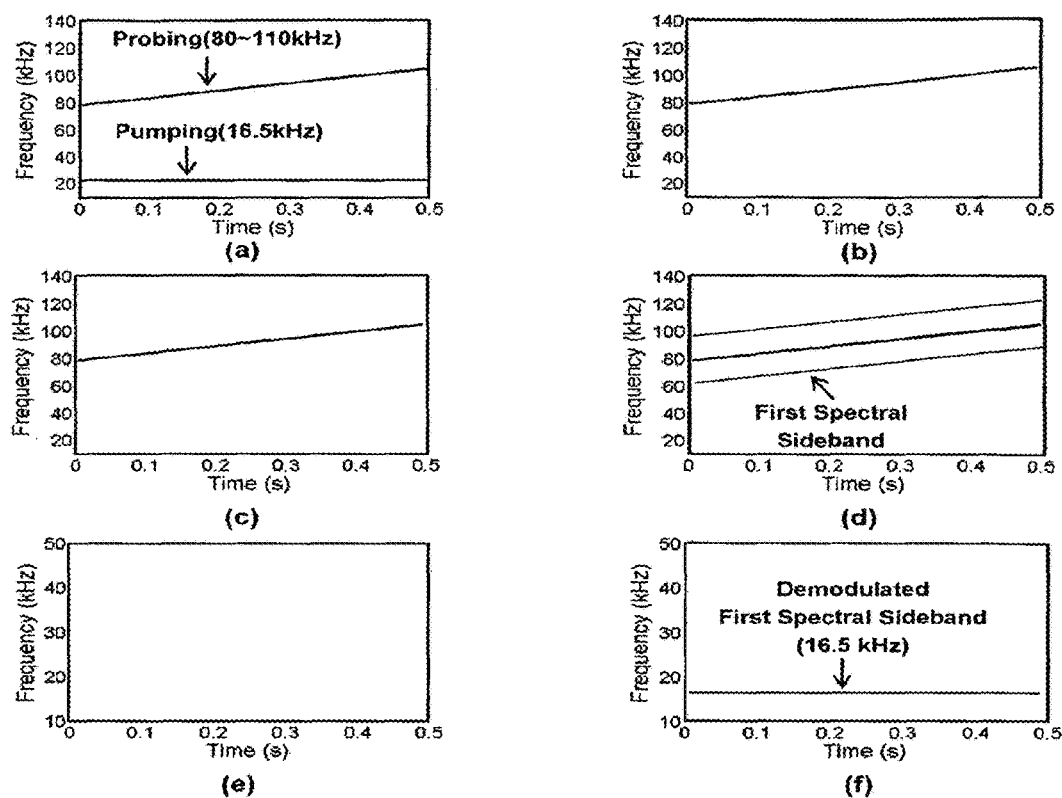
FIG. 5 illustrates an output characteristic according to a signal processing method and whether a structure is damaged or not according to the present invention.

FIG. 5 illustrates an output characteristic of the digitizer 6, the LSR unit 16, and the SD unit 17 according to the LRS and SD signal processing methods and whether the structure is damaged according to the present invention.

FIGS. 5(a) and 5(b) illustrate results obtained by analyzing the signal output (output from the digitizer 6) from a structure with the damage and a structure without the damage in the time-frequency domain, and since there is no large difference according to whether there is the damage, whether there is the damage may not be decided by only the signal output from the structure.

FIGS. 5(c) and 5(d) illustrate results obtained by analyzing the output of the digitizer 6 and the LRS-processed signal in the LSR unit 16 in the time-frequency domain, and the LRS unit 16 generates the first modulation signal from the structure with the damage (see FIG. 5(d)) and does not generate the first modulation signal from the structure without the damage (see FIG. 5(c)). Further, FIGS. 5(e) and 5(f) illustrate signals in which only the first modulation signals are extracted from the output of the digitizer 6 by applying the SD method after the LSR technique to the response of the structure. Since the modulated signal is generated only when the damage is generated, the SD unit 17 may sense the damage of the structure according to whether the modulated signal is generated.

Figure 6:
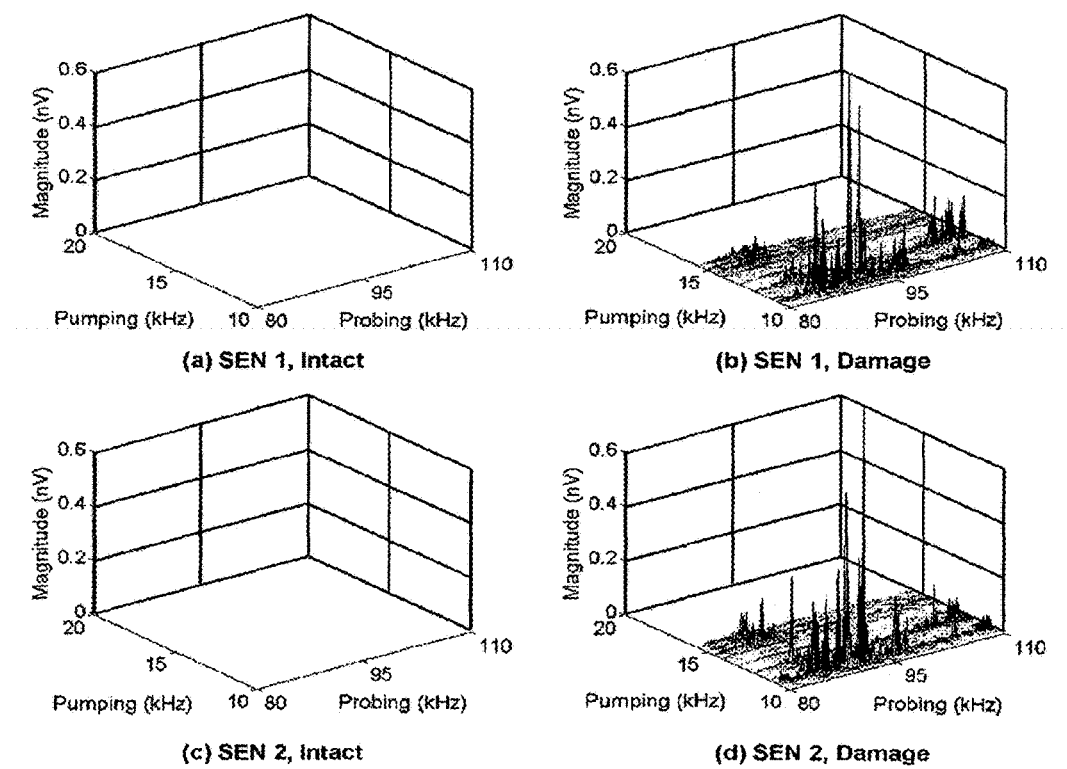
FIG. 6 is an output characteristic of a first sideband spectrogram (FSS) of the present invention.

FIG. 6 illustrates an FSS output characteristic in the frequency band according to the present invention, and it can be seen that the frequency response by the nonlinearity generated in the structure is largely influenced by a combination of frequencies of two ultrasonic waves vibrated for modulation. Accordingly, a signal for the frequency combination in a broad band is measured and thus, the frequency providing the largest output signal is used for the damage diagnosis. As a result, the present invention measures the output signal of the digitizer while fixing the frequency of the probing signal and changing the frequency of the pumping signal, extracts only the first modulation components by LRS and SD processing the measure signal, and generates the FSS by combining the first modulation components for each frequency.

Figure 4:
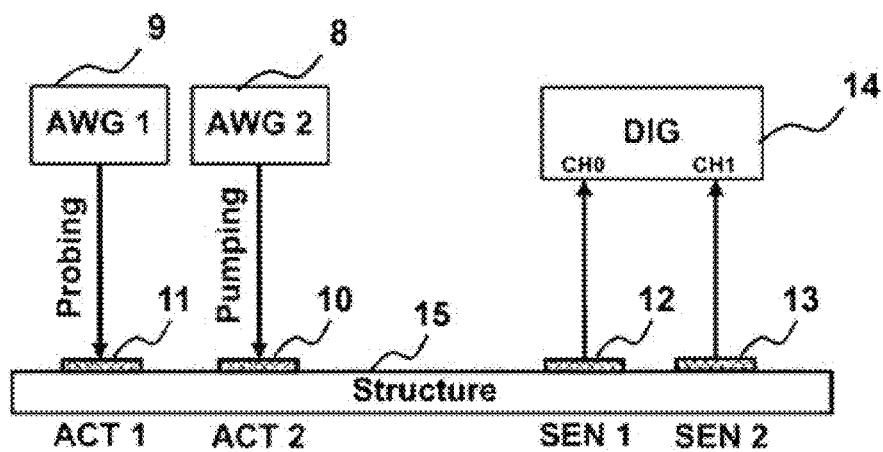
FIG. 4 is a schematic diagram of a measurement system for performing a safety diagnosis test of the structure according to the present invention.

FIG. 4 illustrates a measurement system for performing a safety diagnosis test of the structure according to another embodiment of the present invention, and in the measurement system, a plurality of piezoelectric transducers 12 and 13 are attached in order to outputting the response of the structure unlike FIG. 3 to test whether there is a difference of the measurement result according to a position where the piezoelectric transducers are attached to the structure. In the measurement system of FIG. 4, the piezoelectric transducers sensing the damage of the structure are attached to two different places. It is analyzed that the difference in measured result according to the positions of two piezoelectric transducers 12 and 13 is slight with reference to FIGS. 6 and 7. Since the components (the LSR unit, the SD unit, the FSS generation unit, and the wireless communication unit) after a digitizer 14 are the same as those illustrated in FIG. 3, the description thereof will not be described.

FIG. 6 illustrates the FSS generated by continuously changing a frequency of the pumping signal from 10 to 20 kHz and a frequency of the probing signal from 80 kHz to 100 kHz. FIGS. 6(a) and 6(c) illustrate a measured result of the measurement system illustrated in FIG. 4, and when there is no damage of the structure, the FSS is generated by continuously changing the pumping signal and the probing signal of the signal of the digitizer 14 from a sixth piezoelectric transducer 12 and a seventh piezoelectric transducer 13 for each frequency. When measuring, the frequency of the pumping signal increases by 500 Hz from 10 kHz to 20 kHz, and the frequency of the probing signal is uniformly maintained from 80 kHz to 100 kHz. When there is no damage of the structure, it can be seen that the first modulation component is not generated.

FIGS. 6(b) and 6(d) illustrate results of generating the FSS by continuously changing the pumping signal and the probing signal of the output signal of the FSS generation unit 18 from the sixth piezoelectric transducer 12 and the seventh piezoelectric transducer 13 for each frequency.

Referring to FIG. 6, it may be observed that when there is the damage of the structure, both first modulation components are generated in the sixth piezoelectric transducer 12 and the seventh piezoelectric transducer 13. A specific point is that even though there is the damage of the structure, there is a frequency band in which the modulation component is not generated according to the frequency combination. Accordingly, when the frequency of the pumping signal is set to 10 kHz to 20 kHz and the frequency of the probing signal is set to 80 kHz to 110 kHz, output levels of the first modulation signals according to whether the structure is damaged are significantly different, and thus, whether the structure is damage may be precisely sensed as compared with the existing safety diagnosis method by selecting a frequency of the probing signal from a frequency band of 80 kHz to 110 kHz. As a result, when a diagnosis sensor precisely sensing the fatigue crack of the structure is manufactured, the frequency of the probing signal needs to be selected as the frequency. Generally, it is preferred in the implement of the safety diagnosis apparatus that the frequencies of the pumping signal and the probing signal select the frequency of the signal having the highest output characteristic from the FSS.

Figure 7:
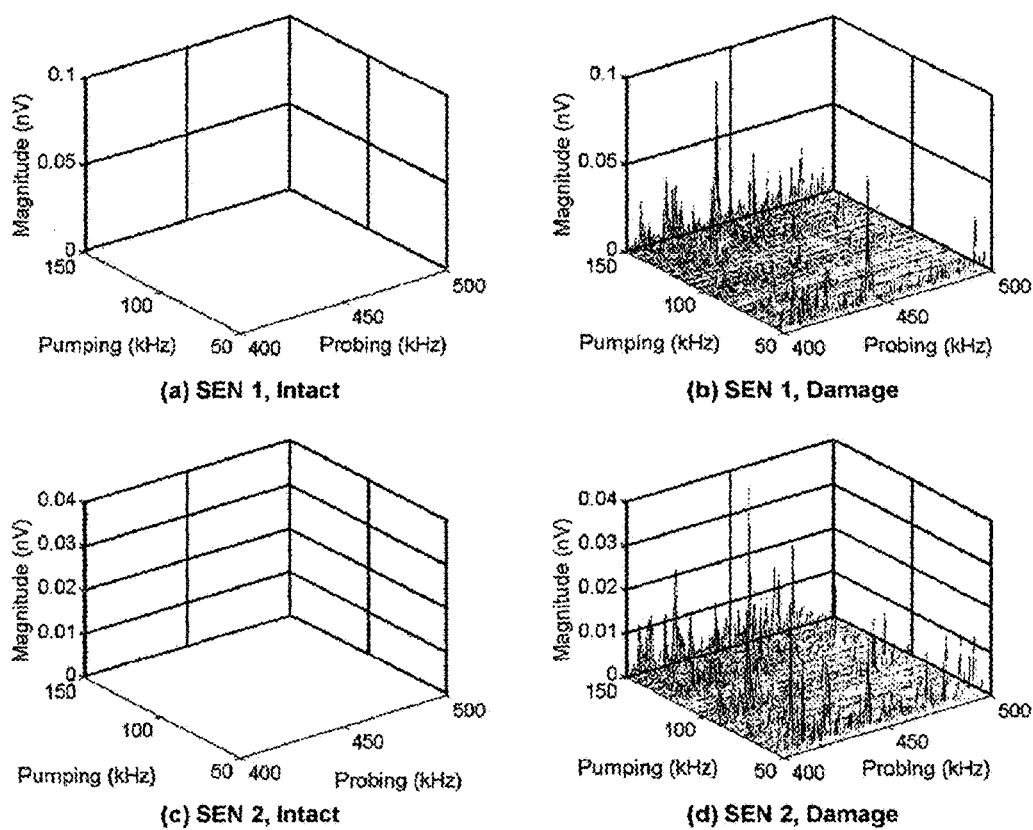
FIG. 7 illustrates an FSS output characteristic in an experimental results of the present invention.

FIG. 7 illustrates a result measured when the frequency of the pumping signal increases up to 50 to 150 kHz and the frequency of the probing signal increases up to 400 to 500 kHz. The frequency increases as compared with the test of FIG. 6, and as a result, a change of the FSS according to where there is the damage is very small as compared with FIG. 6. Accordingly, a diagnosis apparatus using the frequency of FIG. 7 needs to apply a probing signal and a pumping signal to the piezoelectric transducers with large power. Referring to FIG. 7, it can be seen that using the frequency band illustrated in FIG. 6 is advantageous to implement a low-power sensor.

The control unit controls the high frequency generation unit and the low frequency generation unit to output the probing signal and the pumping signal of the corresponding frequency to implement the diagnosis sensor with improved precise according to a temperature and a characteristic of the structure.

Hereinabove, the invention has been described in detail with reference to the embodiments. However, it will be appreciated by those skilled in the art that changes may be made in these embodiments without departing from the principles and spirit of the invention, the scope of which is defined in the appended claims and their equivalents.

INDUSTRIAL APPLICABILITY

The present invention can be widely used as a safety diagnosis apparatus in a safety diagnosis and management field of various metal structures including an infra-structure, an airplane, a train, and the like.

What is claimed is:

1. A safety diagnosis method for a structure using a nonlinear ultrasonic wave modulation technique, the method comprising:
    making the structure vibrate by applying signals of different ultrasonic frequencies;
    converting the responses of the structure generated by the vibration into digital signals;
    extracting first modulation signals by subtracting the harmonic responses and the linear responses of the signals of different ultrasonic frequencies from the digital signals and synchronously demodulating the digital signals;
    constructing a first sideband spectrogram by combining the first modulation signals generated by changing at least one frequency among the signals of different ultrasonic frequencies; and
    deciding whether the structure is cracked based on the first sideband spectrogram.

2. The safety diagnosis method for a structure using a nonlinear ultrasonic wave modulation technique of claim 1, the method further comprising:

after the converting of the responses of the structure generated by the vibration into the digital signals,
    converting the responses generated in the structure into second digital signals by applying one of the frequency signals; and
    converting the responses generated in the structure into third digital signals by applying the other one of the frequency signals.

3. The safety diagnosis method for a structure using a nonlinear ultrasonic wave modulation technique of claim 2, wherein the extracting the first modulation signals includes, a linear response subtracting step of subtracting the second digital signals and the third digital signals from the first digital signals, and extracting the first modulation signals from the digital signals through synchronous demodulation of the signals subtracted with the linear responses.

4. The safety diagnosis method for a structure using a nonlinear ultrasonic wave modulation technique of claim 1, wherein in the making of the structure vibrate by applying signals of different ultrasonic frequencies, one of the signals of different ultrasonic frequencies is applied to the inside of a concentric dual piezoelectric transducer attached to the structure and the other one is applied to the outside of the concentric dual piezoelectric transducer.

5. The safety diagnosis method for a structure using a nonlinear ultrasonic wave modulation technique of claim 1, wherein the deciding of whether the structure is cracked based on the first sideband spectrogram further includes performing a safety diagnosis in real time by wirelessly transmitting whether the structure is damaged to an inspection system which is positioned at a remote place.

6. A method for measuring a fatigue crack of a structure using a nonlinear ultrasonic wave modulation technique, the method comprising:
    applying one of ultrasonic waves of different ultrasonic frequencies to the inside of a concentric dual piezoelectric transducer attached to the structure and applying the other one ultrasonic wave to the outside of the concentric dual piezoelectric transducer to make the structure vibrate;
    converting the responses of the structure generated by the vibration into first digital signals;
    converting the responses of the structure generated by applying only the one ultrasonic wave to the concentric dual piezoelectric transducer into second digital signals;
    converting the responses of the structure generated by applying only the other one ultrasonic wave to the concentric dual piezoelectric transducer into third digital signals; and
    deciding whether the structure is cracked through synchronous demodulation of signals acquired by removing the second digital signals and the third digital signals from the first digitals signals.

7. The method for measuring a fatigue crack of a structure using a nonlinear ultrasonic wave modulation technique of claim 6, wherein the deciding of whether the structure is cracked further includes generating the first modulation signal while continuously changing the frequencies of the ultrasonic waves, constructing a first sideband spectrogram by combining the first modulation signals generated in the respective frequencies, and deciding whether the structure is cracked from the generated first sideband spectrogram.

8. A system for measuring a fatigue crack of a structure using a nonlinear ultrasonic wave modulation technique, the system comprising:

a low-frequency generation unit generating an ultrasonic wave of a low frequency according to a first control signal;
a high-frequency generation unit generating an ultrasonic wave of a high frequency according to a second control signal;
a first piezoelectric transducer attached to the structure to apply the ultrasonic wave of the low frequency to the structure;
a second piezoelectric transducer attached to the structure to apply the ultrasonic wave of the high frequency to the structure;
a third piezoelectric transducer converting the structural responses into electric signals;
a digitizer converting an output of the third piezoelectric transducer into digital signals;
a control unit controlling activation timings of the first control signal and the second control signal; and
a digital signal processing unit subtracting linear responses and harmonic responses from an output of the digitizer and synchronously demodulating the corresponding responses to output the synchronously demodulated responses as fatigue crack information of the structure.

9. The system for sensing a fatigue crack of a structure using a nonlinear ultrasonic wave modulation technique of claim 8, wherein the control unit controls an output frequency of the low-frequency generation unit or an output frequency of the high-frequency generation unit to be varied or signal output timings of the low-frequency generation unit or an output frequency of the high-frequency generation unit to apply both the low frequency and the high frequency, only the low frequency, or only the high frequency to the structure.

10. A wireless diagnosis apparatus for a structure using a nonlinear ultrasonic wave modulation technique, the apparatus comprising:
a frequency generation unit outputting a pumping signal and a probing signal of different ultrasonic frequencies;
a piezoelectric transducer unit making vibration by applying the pumping signal and the probing signal to the structure and outputting responses of the structure as electric signals;
a digitizer converting an output of the piezoelectric transducer unit into digital signals;
a digital signal processing unit constructing a first sideband spectrogram through linear response subtraction and synchronous demodulation of an output of the digitizer; and
a wireless transmission unit wirelessly transmitting the first sideband spectrogram to an inspection system of a remote place.

11. The wireless diagnosis apparatus for a structure using a nonlinear ultrasonic wave modulation technique of claim 10, wherein the digital signal processing unit includes a linear response subtracting unit subtracting the output of the digitizer when only the pumping signal is applied and the output of the digitizer when only the probing signal is applied from the output when both the pumping signal and the probing signal are applied, and a synchronous demodulation unit synchronously demodulating an output of the linear response subtracting unit to generate first modulation signals.

12. The wireless diagnosis apparatus for a structure using a nonlinear ultrasonic wave modulation technique of claim 10, wherein the digital signal processing unit further includes a first sideband spectrogram generation unit constructing a first sideband spectrogram by combining first modulation signals acquired while continuously changing a frequency of the pumping signal or a frequency of the probing signal during a predetermined frequency section.

13. The wireless diagnosis apparatus for a structure using a nonlinear ultrasonic wave modulation technique of claim 10, wherein the control unit sets frequencies corresponding to a first modulation signal having a largest value as the frequency of the pumping signal and the frequency of the probing signal from the first sideband spectrogram.

14. The wireless diagnosis apparatus for a structure using a nonlinear ultrasonic wave modulation technique of claim 10, wherein the piezoelectric transducer unit includes a first piezoelectric transducer attached to the structure to apply the pumping signal to the structure, a second piezoelectric transducer attached to the structure to apply the probing signal to the structure, and a third piezoelectric transducer converting responses of the structure generated by the pumping signal and the probing signal into electric signals.

15. The wireless diagnosis apparatus for a structure using a nonlinear ultrasonic wave modulation technique of claim 10, wherein the frequency of the pumping signal is in the range of 10 to 20 kHz and the frequency of the probing signal is in the range of 80 to 110 kHz.

* * * * *